United States Patent [19]

Gowrylow

[11] Patent Number: 5,017,174
[45] Date of Patent: May 21, 1991

[54] NURSING PAD

[76] Inventor: Felicia B. Gowrylow, 19721 NE. 13th St., Camas, Wash. 98607

[21] Appl. No.: 510,713

[22] Filed: Apr. 18, 1990

[51] Int. Cl.$^5$ .............................................. A41C 3/04
[52] U.S. Cl. ...................................... 450/37; 450/57; 2/267
[58] Field of Search ...................... 450/31, 32, 37, 54, 450/55, 56, 57, ; 2/267

[56] References Cited

U.S. PATENT DOCUMENTS

| | | | |
|---|---|---|---|
| 1,136,727 | 4/1915 | Smith | 450/37 X |
| 2,427,851 | 9/1947 | Gerst | 450/57 |
| 2,454,535 | 11/1948 | Warner | 450/57 |
| 2,627,606 | 2/1953 | DeGrandes | 450/57 |
| 2,767,402 | 10/1956 | Pauk | 450/37 X |
| 2,864,373 | 12/1958 | Buckley | 450/57 |
| 2,891,544 | 6/1959 | London | 450/37 X |
| 3,356,690 | 12/1967 | Plantinga et al. | 450/37 X |
| 3,392,731 | 7/1968 | Silverman | 450/57 |
| 3,399,678 | 9/1968 | Faron | 450/55 |
| 3,502,083 | 3/1970 | Howard et al. | 450/56 |
| 4,047,534 | 9/1977 | Thomaschefsky | 450/37 X |
| 4,074,721 | 2/1978 | Smits et al. | 450/37 X |
| 4,674,131 | 6/1987 | Broel | 450/57 X |
| 4,674,510 | 6/1987 | Sneider | 450/57 |
| 4,700,699 | 10/1987 | Tollerud et al. | 128/156 |
| 4,738,745 | 4/1988 | Fukuzaki et al. | 450/37 X |

FOREIGN PATENT DOCUMENTS 269399  4/1927  United Kingdom .................. 2/267

OTHER PUBLICATIONS

The Natural Baby Company Washable Pad.
100% Cotton Stretch Knit Washable Pad.
The First Years Washable Flannel Pad.
Homemade Rectangular 100% Diaper Flannel Pad.
The American Breast Pads Company Disposable Pad.
Curity Disposable Nursing Pad.
Johnson's Combination Circular and Rectangular Shaped Disposable Nursing Pad.
Gerber Products Company Disposable Pad.
Evenflo Products Company Disposable Pad.

*Primary Examiner*—Werner H. Schroeder
*Assistant Examiner*—Jeanette E. Chapman
*Attorney, Agent, or Firm*—Klarquist, Sparkman, Campbell, Leigh & Whinston

[57] ABSTRACT

A nursing pad for placement inside a cup-like portion of a bra-like garment includes a conical structure of an absorbent material, such as layers of a fabric material or of a paper-like material. The conical structure has an apex, an outer boundary, and a V-shaped portion extending from the apex to the outer boundary, with the absorbent material being overlapped in the V-shaped portion. Preferably threaded stitching, such as zigzag stitching or surger stitching, secures the absorbent material overlapped in the V-shaped portion and around the outer boundary.

13 Claims, 8 Drawing Sheets

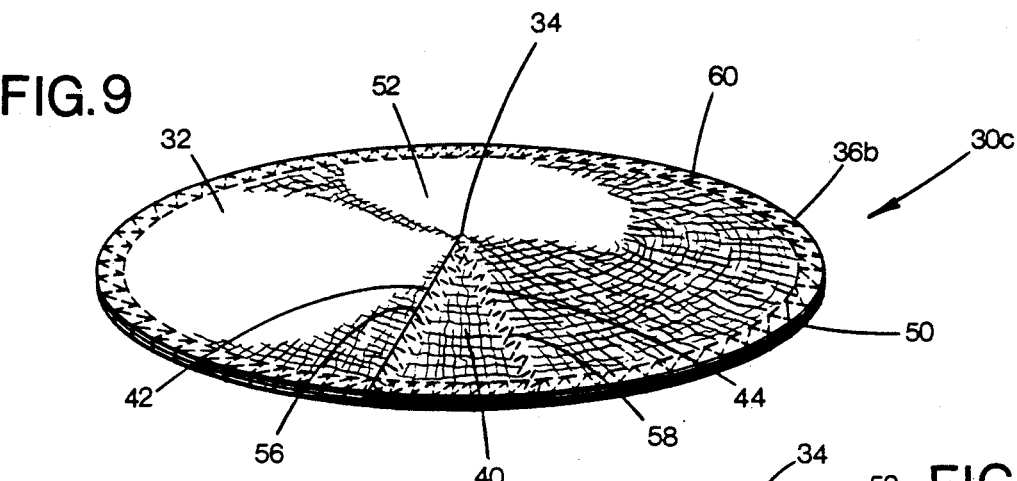
FIG.9
FIG.12
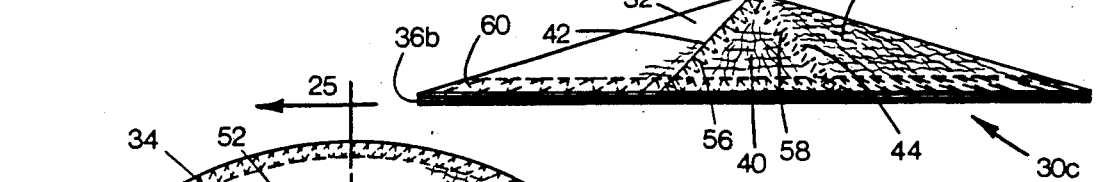
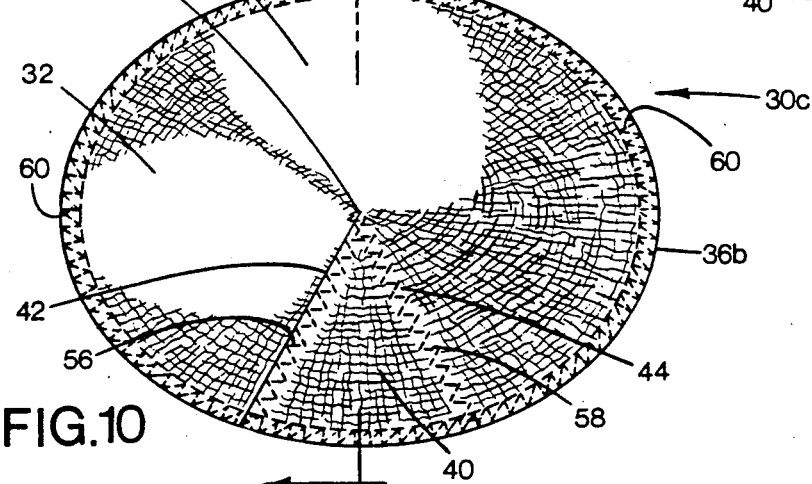
FIG.10
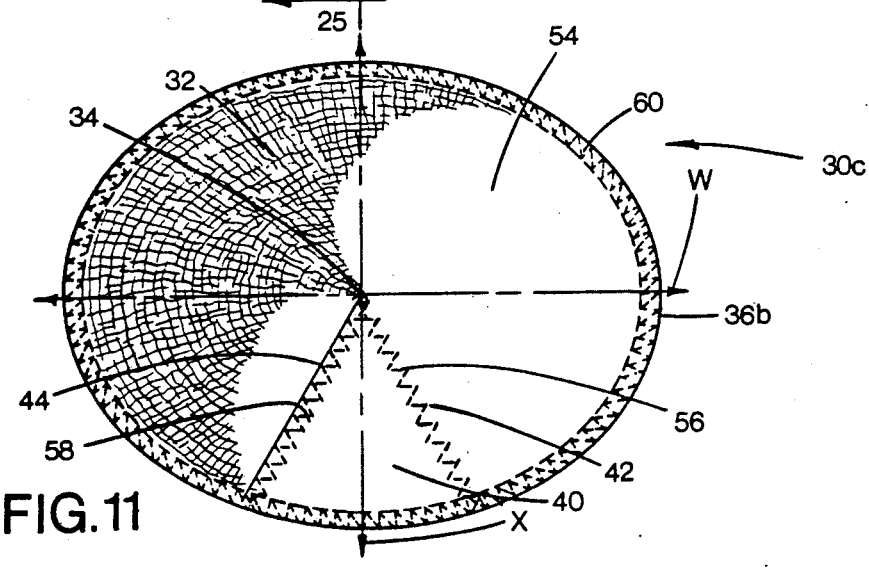
FIG.11

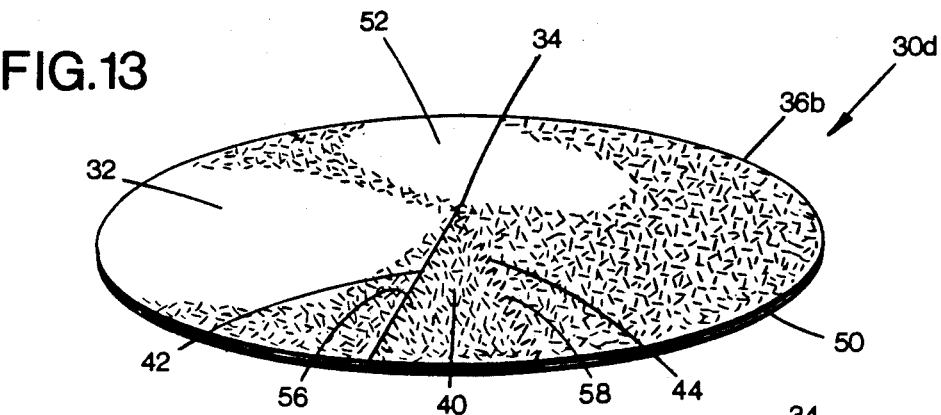
FIG.13
FIG.16
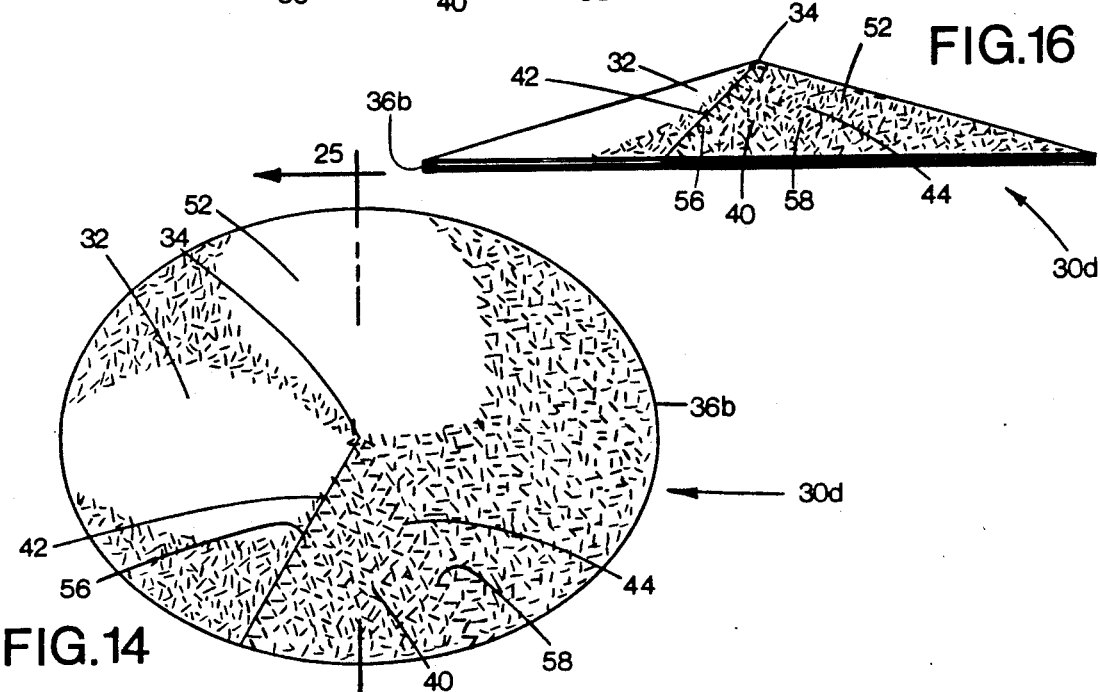
FIG.14
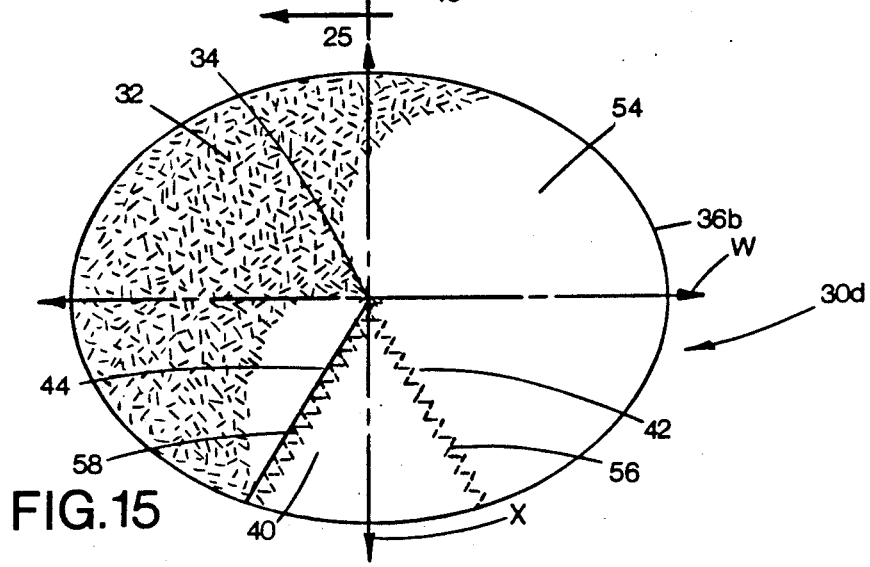
FIG.15

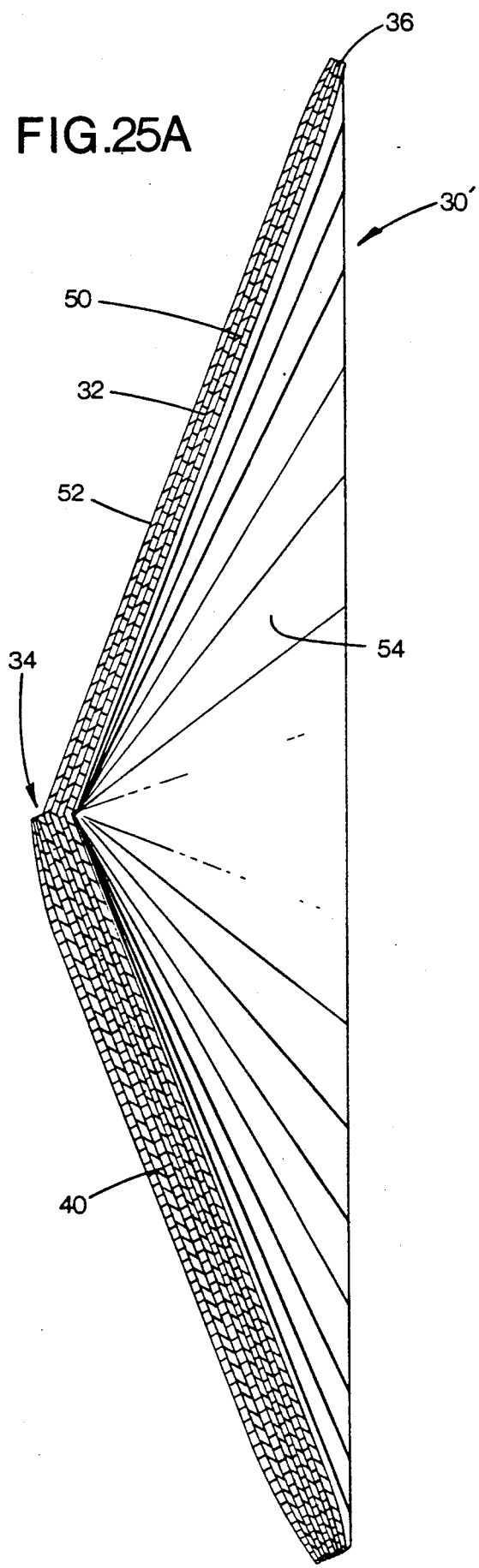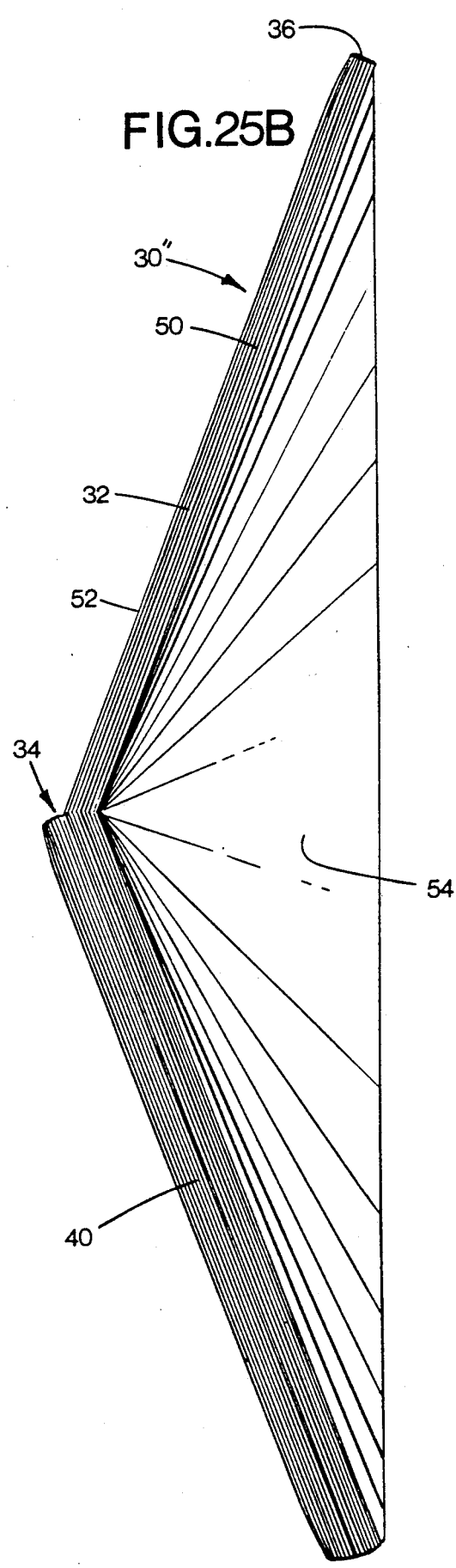

NURSING PAD

BACKGROUND OF THE INVENTION

The present invention relates generally to a nursing pad which may be used by a woman during the lactation period of nursing a baby to absorb milk excretion from the woman's nipples, and more particularly to an improved nursing pad.

A variety of nursing pads comprising various layers of absorbable materials have been made and used by others. For example, the inventor is aware of four types of fabric nursing pads which may be washed between successive uses.

The first of the washable pads is made by the Natural Baby Company and is a flat, circular pad having seven layers of 100% cotton flannel fabric sewn around the periphery with a surger. A second washable pad has circular periphery and is formed by five layers of a 100% cotton stretch knit fabric with a surger hem about the periphery. A third known washable pad is sold under the registered trademark THE FIRST YEARS and includes three fabric layers having a circular periphery with surger stitching around the periphery. The fabric layers of THE FIRST YEARS pad include a first outer layer of 100% cotton, a second outer layer of 100% polyester, and a lining layer of 100% olefin between the outer layers. A fourth known washable pad is homemade and generally rectangular in shape. This homemade pad has six layers of 100% diaper flannel, with a zigzag stitching around the periphery of the pad.

The inventor is aware of five types of disposable nursing pads.

The first disposable pad is sold by the American Breast Pads Company, and is commonly available at J.C. Penney stores. This pad is circular and includes 18 layers of a very thin crepe paper sandwiched between two opposing outer layers of a nonwoven moisture-pervious paper. The layers are secured together by two parallel rows of chain stitching, with each row located along a chord of the circle defining the pad periphery. The parallel rows of chain stitching are equidistantly spaced from the center and located near the outer edges of the pad. This pad has a thumbprint-sized depression in the center of one side of the pad. The second known disposable nursing pad is sold under the registered trademark CURITY. The CURITY pad is circular and includes a soft absorbent top sheet, an outer plastic sheet, and inner layers of a cotton-like fluff material having a plurality of radially-directed channels extending from a central region of the pad toward the outer periphery. During wearing a woman, the outer plastic layer of the CURITY pad disadvantageously tends to rustle and crinkle making embarrassing sounds when the woman moves or stretches her arms. Furthermore, the plastic outer layer inhibits the evaporation of absorbed moisture from the pad. As the moisture trapped in the inner fluff layer cools to room temperature, the pads are cold, damp and uncomfortable to wear.

A third disposable nursing pad is sold under the JOHNSON'S trademark and is of a combination circular and rectangular shape. That is, two opposing sides are straight, parallel chords truncating a circular shape, and the remaining two opposing sides are arcuate, having a common radius centered at the center of the pad. The JOHNSON'S pad has a plurality of absorbent layers and what is believed to be a moisture-impervious outer layer. This outer layer includes an adhesive strip to hold the pad securely in place against the inside of a woman's bra. Once again, the moisture-impervious outer layer may disadvantageously rustle and crinkle during wear, causing embarrassing sounds. Furthermore, the adhesive strip may leave adhesive residue on the bra.

A fourth disposable nursing pad is made by the Gerber Products Company. The GERBER pad includes a special embossed design comprising six T-shaped radial spokes extending outwardly from a central region of the pad, with the top portion of the T-shape being at the periphery of the pad. The GERBER pad is circular in shape and includes a moisture-proof barrier shield outer layer.

The fifth known nursing pad is supplied by the Evenflo Products Company and is circular in shape. The EVENFLO pad includes a one-way moisture shield inner layer to be worn against the skin and which lets wetness enter the pad but not flow back to the skin. The pad also includes a breathable moisture barrier outer layer which protects clothing while letting air flow back through the pad to the skin. In between these two outer layers are multiple layers of a high-absorbency type of crepe paper that draws moisture away from the skin. Similar to the pad sold by the American Breast Pads Company, discussed above, the EVENFLO pad has a central thumbprint-sized depression on the inner layer side, and layers secured together by two rows of parallel stitching.

While some disadvantages have been discussed above, all of these known flat pads suffer several additional disadvantages. To state the obvious, a woman's breast is not flat, but generally of a conical nature, and these known flat pads must wrinkle to form a conical shape when worn. These wrinkles are often clearly and embarrassingly evident under a woman's blouse or dress, particularly if the garment is made of a stretch knit material or closely-fitting design.

Furthermore, in between nursings, a woman's breasts actually change shape and texture. After nursing, the breasts are empty and rather soft, then as milk is replenished, they become larger and firmer. So in addition to a woman's movement during an active day, the actual changes in the shape and texture of the breast itself tends to cause these known flat nursing pads to slip and move. The flat pads have a tendency to move into alignment against a flat surface, such as the side of a woman's breast, which may allow milk to embarrassingly leak through the woman's undergarment and outer clothing. In the worst case, the pads can work themselves completely out of the bra, and if the blouse is not tucked in, the pads may actually fall out of the blouse, creating an extremely embarrassing situation for the woman.

Thus, nursing mothers are faced with a variety of embarrassing and aggravating situations when using the currently-available flat nursing pads. A pregnant woman near the latter stages of pregnancy may also use nursing pads to absorb excretions from the nipples. Either woman may be particularly self-conscious concerning the personal nature of these bodily functions and anything tending to unnecessarily draw attention to these functions, such as the rustling, noisy pads or the wrinkles under clothing, can be particularly annoying.

Therefore, a need exists for an improved nursing pad which is not susceptible to the above limitations and disadvantages.

SUMMARY OF THE INVENTION

It is an overall object of the present invention to provide an improved nursing pad for placement inside a cup-like portion of a bra-like garment.

A further object of the present invention is to provide an improved method of forming a washable and reusable nursing pad. Another object of the present invention is to provide an improved nursing pad which fits smoothly under a woman's garments.

Still another object of the present invention is to provide a nursing pad which is self-aligning, and tends to maintain a correct position within the cup-like portion of a bra-like garment during wearing.

Yet another object of the present invention is to provide a nursing pad which does not make embarrassing rustling or crinkling noises when worn.

A further object of the present invention is to provide a nursing pad with increased moisture-absorbency characteristics along one portion thereof.

Another object of the present invention is to provide a nursing pad with enhanced moisture absorbency and moisture evaporation characteristics.

According to one aspect of the present invention, the nursing pad includes a conical structure of an absorbent material. The conical structure has an apex, an outer boundary, and V-shaped portion extending from the apex to the outer boundary. The absorbent material is overlapped in the V-shaped portion. The pad also includes threaded stitching means for securing the absorbent material overlapped in the V-shaped portion. In one illustrated embodiment, the absorbent material is an absorbent paper-like material which allows the nursing pad to be disposed of after use. In an alternate embodiment, the absorbent material is an absorbent fabric material so that the nursing pad may be laundered between successive uses and reworn. According to a further aspect of the present invention, a method is provided of forming a washable nursing pad. This method includes the steps of cutting multiple pieces of a fabric material to a predetermined shape having an outer edge and a central region. The method also includes the step of slitting each of the multiple pieces of fabric with a slit extending from the outer edge to the central region. In a layering step, each of the multiple pieces of fabric is layered to form a layered pad. In an overlapping step, the layers of the fabric adjacent one side of the slit are overlapped over the layers of fabric adjacent the opposite side of the slit to form an overlapped portion of the layered pad. The overlapped portion has boundaries which are defined by said one side and said opposite side of the slit. In a sewing step, the multiple pieces of fabric of the layered pad are sewn together along the overlapped portion boundaries. In a finishing step, the layered pad is finished by sewing together the outer edges of each of the multiple pieces of fabric.

These and other objects, features and advantages of the present invention will become apparent to those skilled in the art from the following description and drawings.

BRIEF DESCRIPTION OF THE DRAWINGS

FIG. 9 is a perspective view of one form of a third embodiment of a nursing pad of a fabric material;

FIG. 10 is a top plan view of the nursing pad of FIG. 9;

FIG. 11 is a bottom plan view of the nursing pad of FIG. 9;

FIG. 12 is a front elevational view of the nursing pad of FIG. 9;

FIG. 13 is a perspective view of one form of a fourth embodiment of a nursing pad of a disposable paper material;

FIG. 14 is a top plan view of the nursing pad of FIG. 13;

FIG. 15 is a bottom plan view of the nursing pad of FIG. 13;

FIG. 16 is a front elevational view of the nursing pad of FIG. 13;

FIGS. 25A and 25B are enlarged sectional views of alternate embodiments of a nursing pad of the present invention taken along lines 25—25 of FIGS. 2, 6, 10, 14, 18 and 22.

DETAILED DESCRIPTION OF PREFERRED EMBODIMENTS

Figure 1:
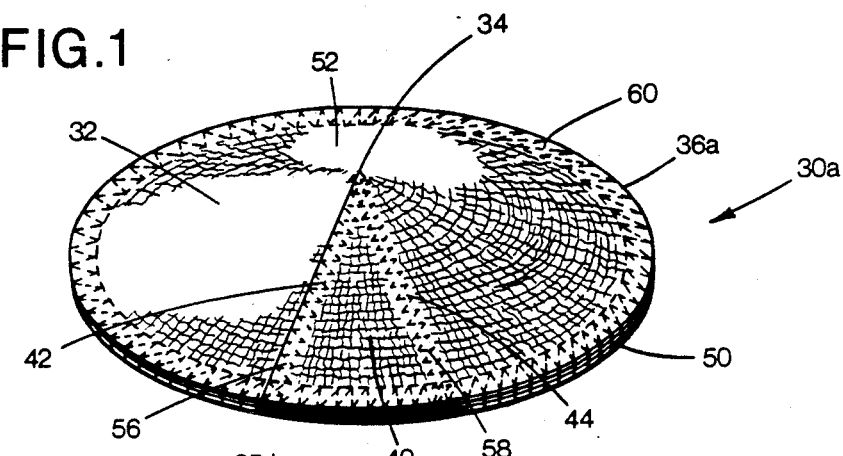
FIG. 1 is a perspective view of one form of a first embodiment of a nursing pad of a fabric material.
Figure 2:
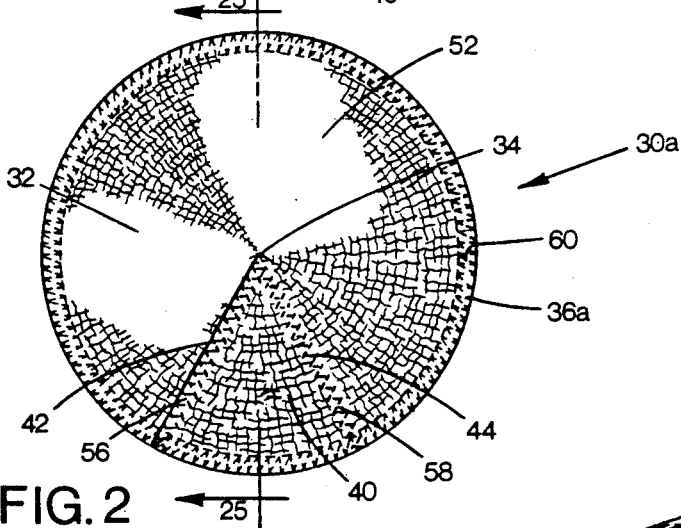
FIG. 2 is a top plan view of the nursing pad of FIG. 1.
Figure 4:
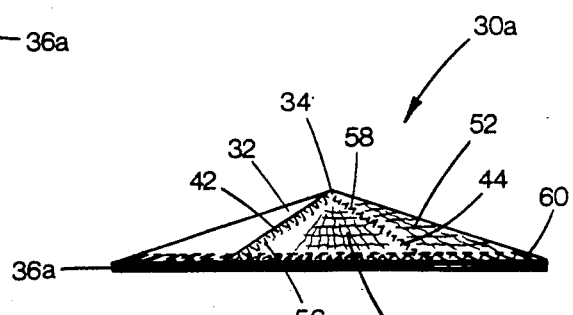
FIG. 4 is a front elevational view of the nursing pad of FIG. 1.
Figure 3:
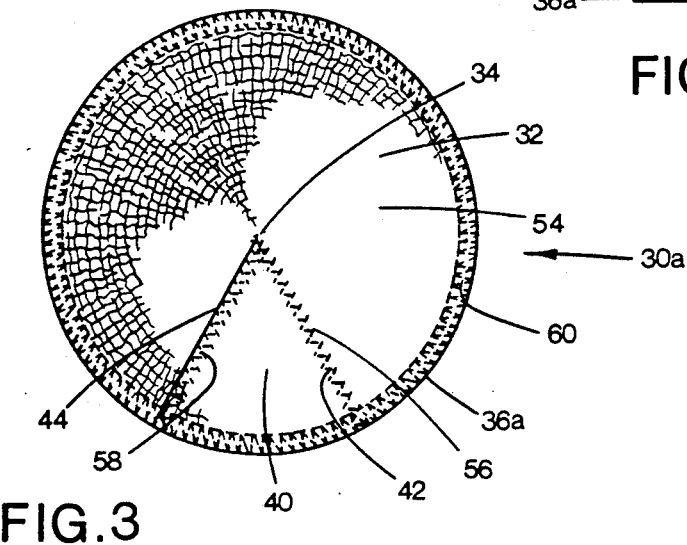
FIG. 3 is a bottom plan view of the nursing pad of FIG. 1.
Figure 5:
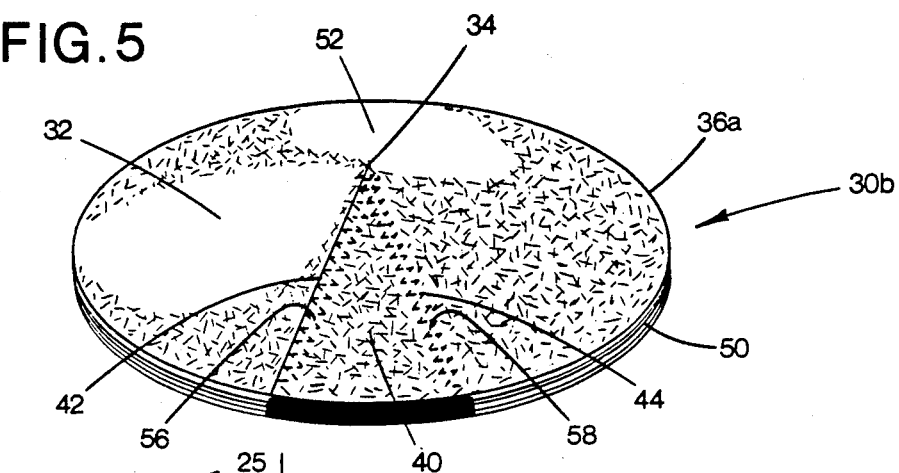
FIG. 5 is a perspective view of one form of a second embodiment of a nursing pad of a disposable paper material.
Figure 6:
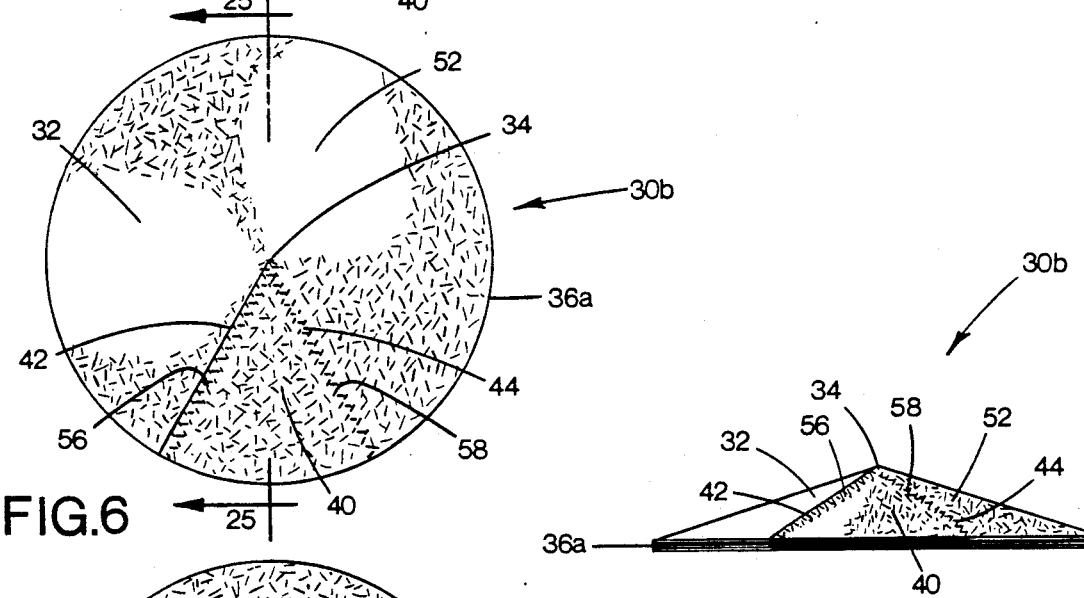
FIG. 6 is a top plan view of the nursing pad of FIG. 5.
Figure 8:
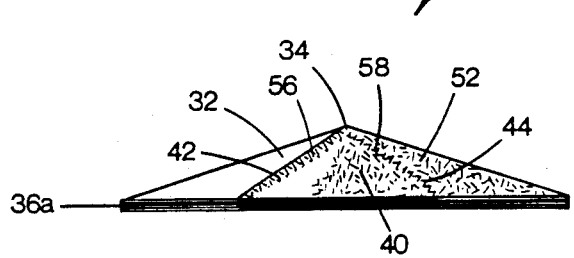
FIG. 8 is a front elevational view of the nursing pad of FIG. 5.
Figure 7:
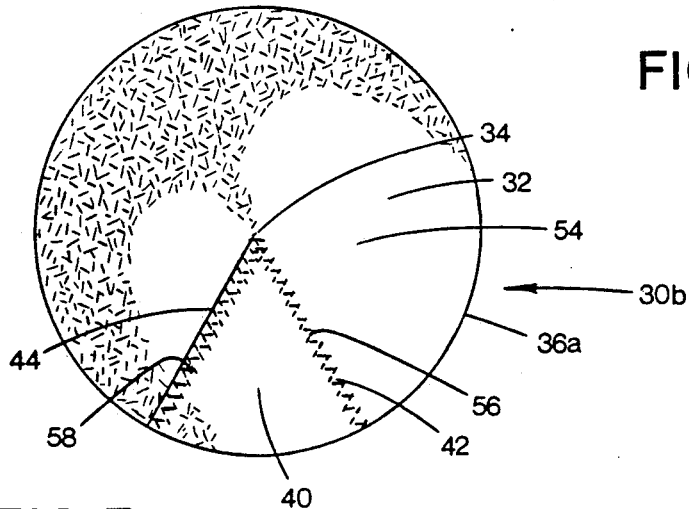
FIG. 7 is a bottom plan view of the nursing pad of FIG. 5.
Figure 17:
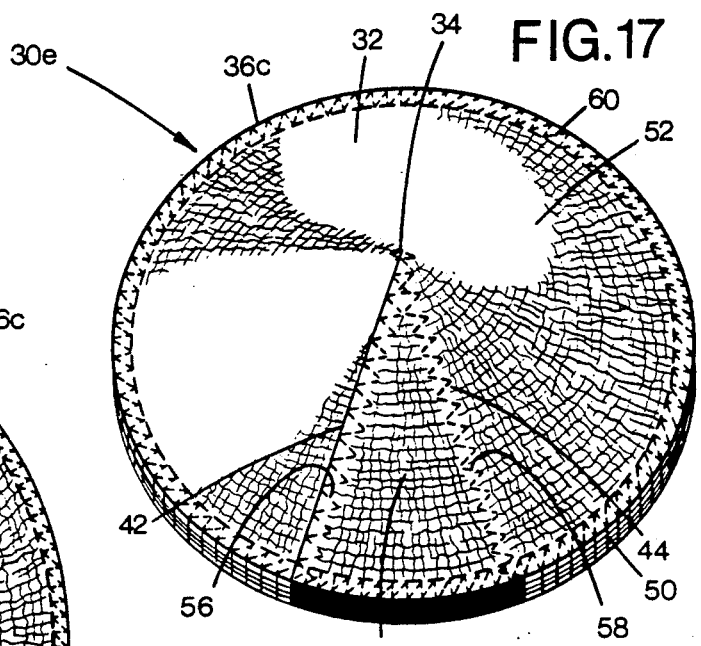
FIG. 17 is a perspective view of one form of a fifth embodiment of a nursing pad of a fabric material.
Figure 18:
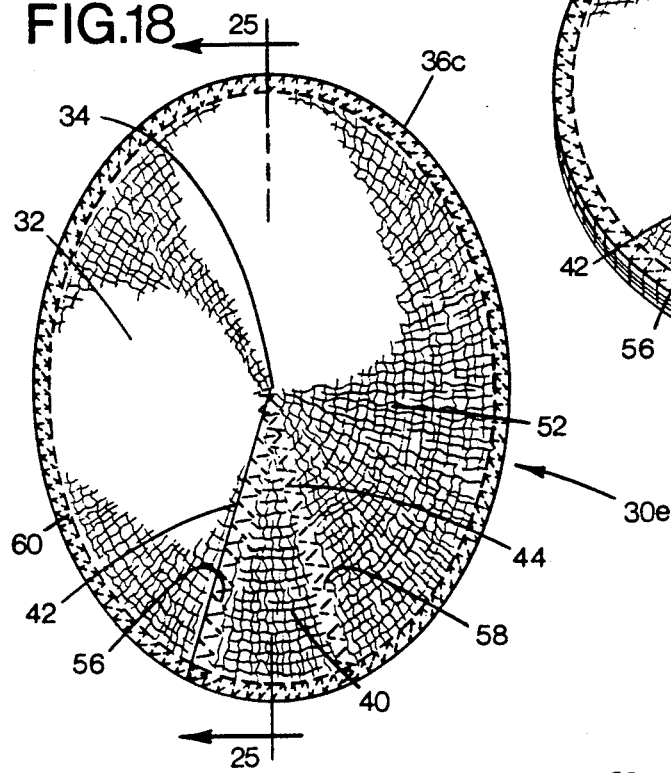
FIG. 18 is a top plan view of the nursing pad of FIG. 17.

An illustrative first embodiment of a nursing pad 30a is shown in FIGS. 1–4, a second embodiment 30b in FIGS. 5–8, a third embodiment 30c in FIGS. 9–12, a fourth embodiment 30d in FIGS. 13–16, a fifth embodiment 30e in FIGS. 17–20, and a sixth embodiment 30f in FIGS. 21–24. The nursing pads shall be collectively designated as "30" hereinafter when discussing general features common to each of the illustrated embodiments. All other item number designations without letters shall refer to features which are common to each of these embodiments.

The nursing pad 30 is illustrated as a conical structure having a main body portion 32 and an apex 34 located in a central region of the main body 32. The nursing pad 30 also has an outer boundary 36 and a V-shaped portion 40, surrounded by the main body portion 32. The V-shaped portion 40 is defined by a V-shaped boundary having first and second legs 42 and 44 joined together near the apex 34 and extending outwardly to the outer boundary 36.

The illustrated nursing pads 30 have a curved outer boundary 36 to provide a smooth fit when worn. Specifically, the nursing pads 30a and 30b each have a generally circular-shaped outer boundary 36a. The nursing pads 30c and 30d each have a substantially elliptical-shaped outer boundary 36b defining mutually perpendicular longitudinal major and transverse minor diameters W and X, respectively, as illustrated in FIGS. 11 and 15. The V-shaped portion 40 of pads 30c and 30d is located substantially symmetrically about the transverse minor diameter X, so pads 30c and 30d may be referred to as horizontally elliptical pads.

Figure 19:
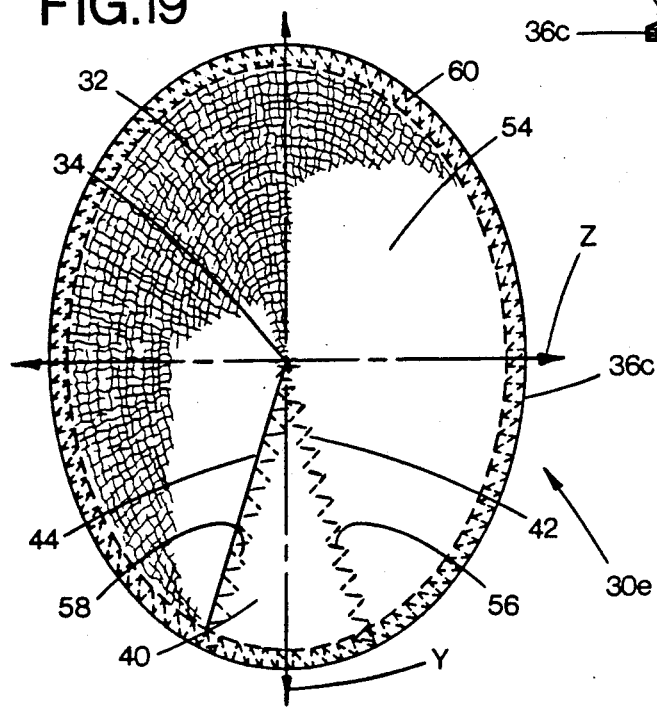
FIG. 19 is a bottom plan view of the nursing pad of FIG. 17.
Figure 20:
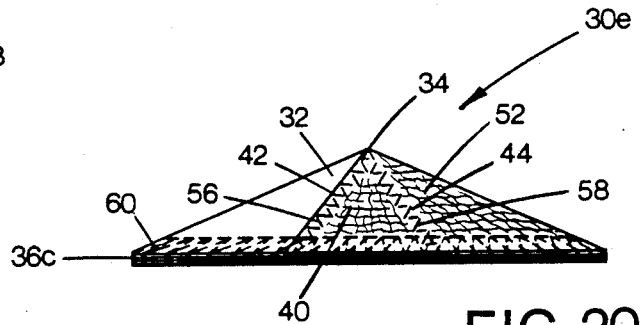
FIG. 20 is a front elevational view of the nursing pad of FIG. 17.
Figure 21:
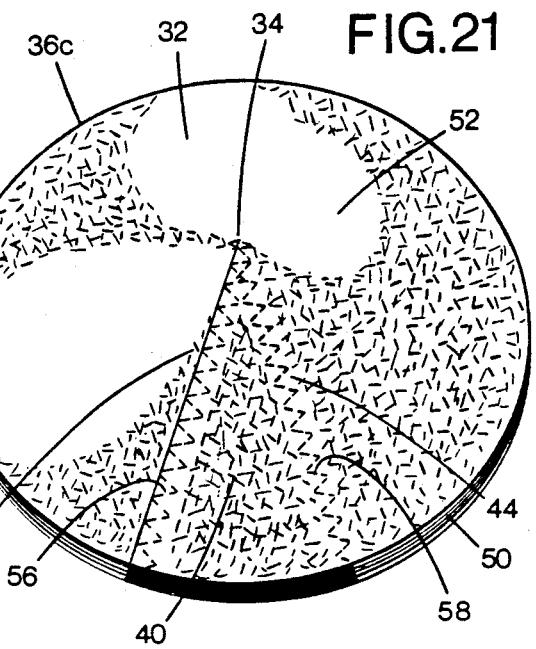
FIG. 21 is a perspective view of one form of a sixth embodiment of a nursing pad of a disposable paper material.
Figure 22:
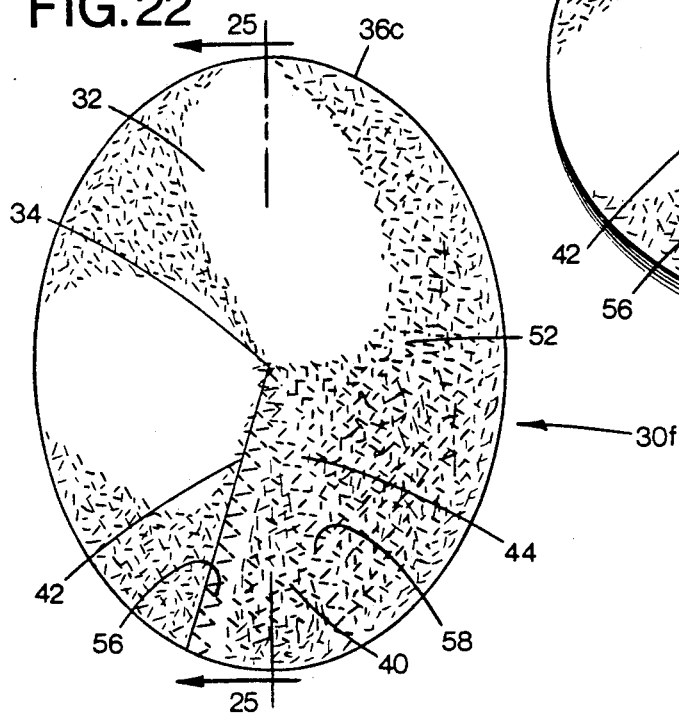
FIG. 22 is a top plan view of the nursing pad of FIG. 21.
Figure 24:
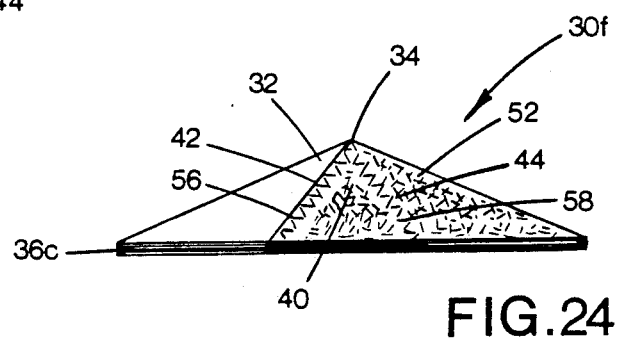
FIG. 24 is a front elevational view of the nursing pad of FIG. 21.
Figure 23:
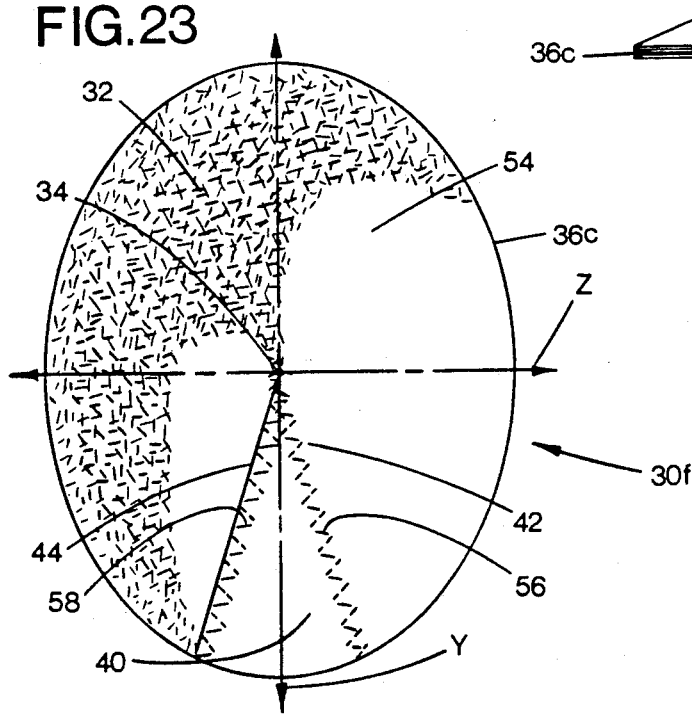
FIG. 23 is a bottom plan view of the nursing pad of FIG. 21.

The nursing pads 30e and 30f each have a substantially elliptical-shaped outer boundary 36c defining mutually perpendicular longitudinal major and transverse minor diameters Y and Z, respectively, as illustrated in FIGS. 19 and 23. The V-shaped portion 40 of pads 30e and 30f is located substantially symmetrically about the longitudinal major diameter Y, so pads 30e and 30f may be referred to as vertically elliptical pads.

The nursing pad 30 is formed by a plurality of layers 50 of an absorbent material, including an outer layer 52 forming an outer convex surface and an inner layer 54 forming an inner concave surface. In the illustrated embodiment, the number of layers 50 in the V-shaped portion 40 are twice the number of layers in the main body portion 32 which advantageously provides an increased moisture absorbency characteristic to the V-shaped portion of the pad. The number of layers 50 in the main body portion 32 depends upon the absorbency characteristics of the absorbent material chosen and the degree of absorbency desired.

As illustrated by nursing pads 30a, 30c and 30e, the absorbent material of layers 50 may be an absorbent fabric, such as a diaper flannel or similar soft material, a birdseye weave fabric, such as a gauze or a cheesecloth weave type of fabric or the like, or a combination thereof. The fabric may be woven or of a stretch knit construction. Preferably, the inner layer 54 is of a soft diaper flannel, while the remaining layers are of a birdseye weave fabric.

For example, satisfactory results have been obtained when the inner layer 54 is of a diaper flannel and the remaining layers are of a cheesecloth weave, comprising between three and seven layers in the main body portion 32. In the V-shaped portion 40, the fabric may be overlapped in a manner discussed further below, yielding eight to sixteen layers in the V-shaped portion depending upon the number of layers in the main body portion 32. As shown in FIG. 25A, the nursing pad 30' has four layers in the main body portion 32, and eight layers in the V-shaped portion 40. The nursing pad 30" shown in FIG. 25B has a main body portion 32 with eight layers and a V-shaped portion 40 with 16 layers.

As illustrated by nursing pads 30b, 30d and 30f, the absorbent material of layers 50 may be an absorbent paper-like sheet material, such as a crepe-type of paper, so the nursing pad may be disposed of after use. Selecting a suitable type of paper-like sheet material, or a combination of plural types of paper-like sheet material, to implement the present invention is well within the capabilities of one skilled in the art as evidenced from the known types of disposable pads discussed above in the Background portion of this specification. In the V-shaped portion 40, the layers 50 of the selected paper-like sheet material may be overlapped in a manner discussed further below such that there are twice the number of layers in the V-shaped portion as in the main body portion 32.

The nursing pad 30 also includes attachment means along each leg 42 and 44 of the V-shaped boundary, such as threaded stitching means which may be surger stitching, zigzag stitching or the like, 56 and 58 along respective legs 42 and 44. The pad 30 may also include boundary attachment means, which are preferably boundary threaded stitching means, such as surger stitching, zigzag stitching or the like, 60 extending around the outer boundary 36 of the pad 30. The surger stitching 60 serves to secure the edges of the fabric together and retard any unraveling of the fabric layers.

Alternatively, the nursing pads 30b, 30d and 30f having layers 50 of a paper-like sheet material may have attachment means 56, 58 and 60 comprising bonding means (not shown) of an adhesive. The particular type of adhesive may be selected by one skilled in the art depending upon various factors such as curing time, non-solubility upon exposure to milk excretion, and the type of paper-like sheet material selected to implement the present invention.

While some users may prefer the disposable convenience of the paper nursing pads 30b, 30d and 30f, others may prefer to use the fabric nursing pads 30a, 30c and 30e. For example, some of the earlier disposable pads discussed above in the background of the invention section have been known to leave paper residue on a woman's nipple after use. Before allowing the baby to nurse, this paper residue must first be wiped from the nipple. This may be particularly inconvenient, since often a damp cloth is required to wipe away the residue. This time-consuming cleaning process can be particularly annoying if the baby is hungry and fussing.

Furthermore, a nursing woman's nipple is known to provide a natural sterilizing process for the nipple, and this process is disrupted by the sticking paper residue. While there are types of paper-like materials which will not stick to a wet nipple, as evidenced by some of the earlier disposable nursing pads discussed above, the fabric nursing pads, such as 30a, 30c and 30e, advantageously do not leave such residue on the nipple.

The fabric nursing pads 30a, 30c and 30e have a softer feel than some of the earlier disposable paper pads. Thus, the fabric pads may feel more comfortable to wear, especially if the woman's nipples have become sore, cracked or chapped from nursing, such as may occur after the baby is born when nursing is first started. Comfort at this stage is particularly important to encourage the mother to continue nursing the baby, and thereby allow the baby to receive the known benefits of natural mother's milk, as opposed to commercially prepared formulas or cow's milk. After several months of nursing, a woman may find that there is less leakage between nursings, and her nipples have become tougher and adapted to the demands of the nursing baby. Thus, during these latter stages of the nursing experience, a woman may find the paper nursing pads 30b, 30d and 30f to perform comparably with fabric nursing pads 30b, 30d and 30f.

Figure 26:
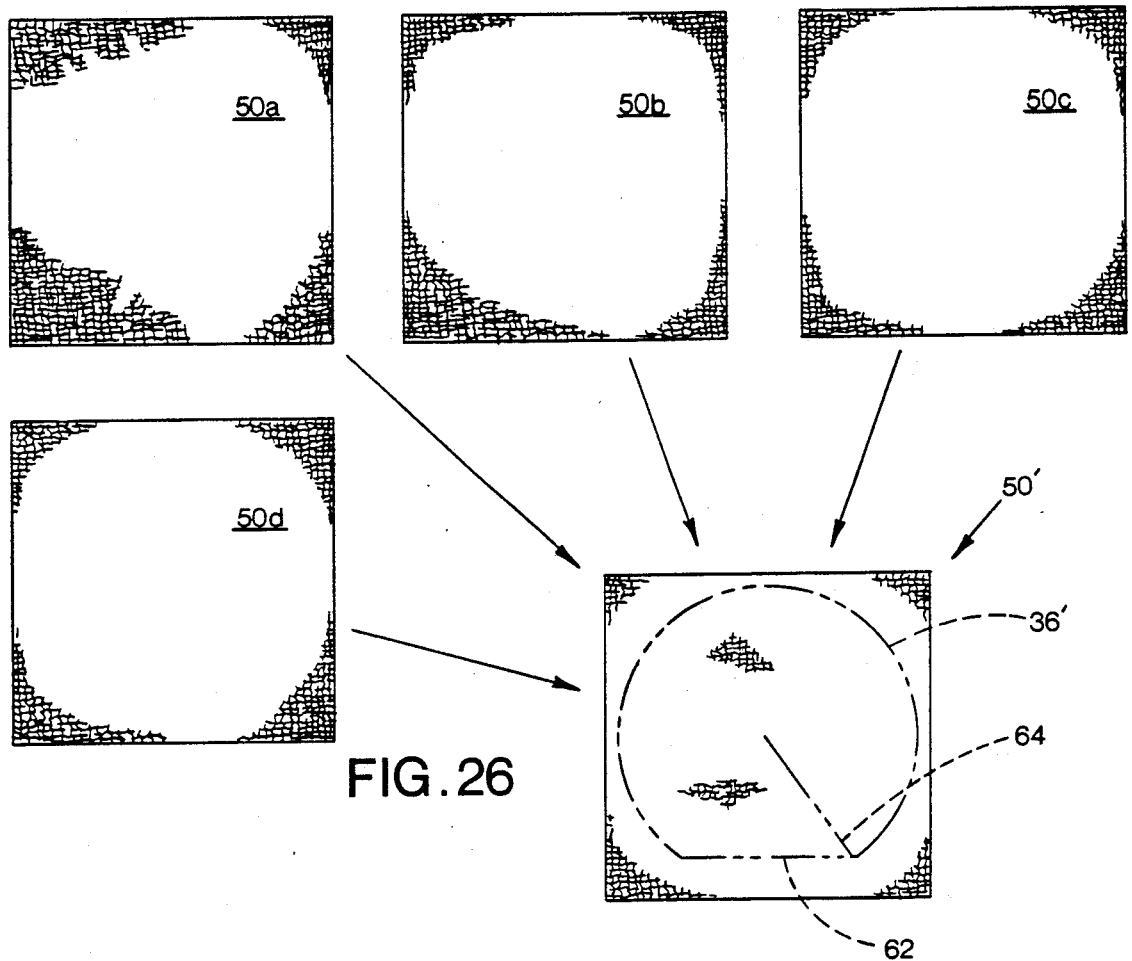
FIGS. 26–28 illustrate one method of forming one form of a nursing pad of the present invention.
Figure 27:
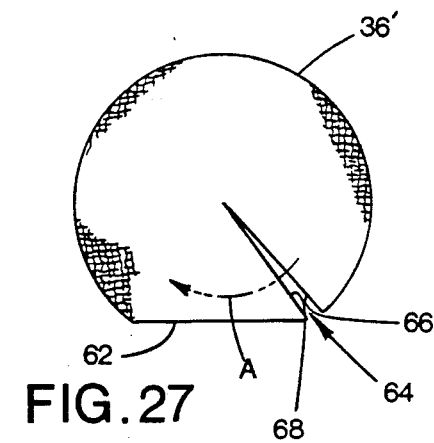
Figure 28:
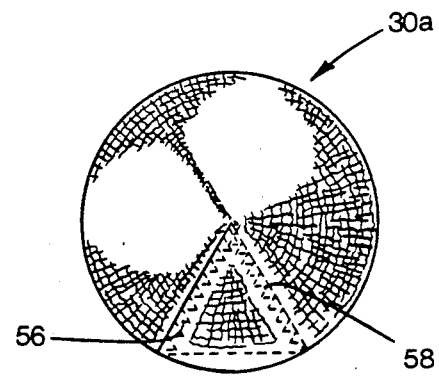

A method of forming a washable nursing pad, such as nursing pads 30a, 30c and 30e, is illustrated in FIGS. 26–28 and includes the following steps. In FIG. 26, multiple pieces of a fabric material 50a, 50b, 50c and 50d are shown as being layered to form a layered structure 50'. The layered multiple pieces of fabric are cut according to a pattern to a predetermined shape having an outer edge 36' and a central region corresponding to the central region of an assembled pad. The illustrated outer edge 36' corresponds to the nursing pad 30a having a circular outer edge 36a and preferably includes a straight edge 62. The multiple pieces of fabric are each slit with a slit 64 extending from the outer edge 36' to the central region and having opposing first and second sides 66 and 68 (see FIG. 27). In the illustrated embodiment, the slit 64 is located along the straight edge 62, and preferably begins at the outer edge 36' near one end of the straight edge 62 as shown.

The order of the layering, cutting and slitting steps may vary. For example, the individual layers of fabric 50a, 50b, 50c and 50d may each be individually cut to the predetermined shape and slit followed by steps of layering and aligning the slits (and straight edges if used) to form the layered pad of FIG. 27. Alternatively, the layers of fabric 50a, 50b, 50c and 50d may first be layered to form the layered structure 50', and the cutting and slitting steps combined, such as by a dye cutting through all of the fabric layers in one stroke. Alternatively, scissors could be used to cut and slit the fabric layers by hand. The conical shape of the nursing pad 30 may be formed by overlapping the layers of fabric adjacent slit side 66 over the layers of fabric adjacent the opposite slit side 68 in the direction indicated by arrow A in FIG. 27. In this manner, the overlapped V-shaped portion 40 forms a dart with the slit side 66 forming leg 42 of the V-shaped portion defining boundary, and slit side 68 forming the other leg 44 of the V-shaped defining boundary. In the illustrated embodiment, the overlapped V-shaped portion spans approximately sixty degrees of arc in the finished pad 30.

In a sewing step, the overlapped V-shaped portion 40 is secured in place by sewing together the multiple pieces of fabric along the V-shaped boundary legs 42 and 44 to form the respective corresponding legs 56 and 58 of the threaded stitching attachment means, as shown in FIG. 28. A feathering step may be included at this point, wherein the fabric lying along the outer edge 36' is adjusted to lie smoothly, such as by pressing together and smoothing or feathering the outer layers by hand to lie smoothly and evenly.

In a finishing step, the layered pad is sewn together along the outer edge 36' to form the boundary attachment means 60, and thereby form the nursing pad 30a as illustrated in FIGS. 1-4. It is apparent that by varying the predetermined shape of the outer edge 36', nursing pads 30 may be formed having outer boundaries 36 of alternate shapes, such as the outer boundary 36b of nursing pad 30c, or outer boundary 36c of nursing pad 30e. Furthermore, additional stitching may be included across the main body portion 32 or the V-shaped portion 40 of the pad if desired.

It is apparent that the nursing pads 30b, 30d and 30f may also be formed in the manner described above if threaded stitching means are to be used as the attachment means. Although the nursing pads 30b, 30d and 30f are shown without outer boundary threaded stitching means 60, such stitching may also be included if desired, or alternatively, the outer edges may be secured together by bonding means. Bonding means may also be used for the attachment means along the V-shaped boundary. After an overlapping step as described above with respect to the fabric pads, a bonding step is performed to secure the edges 66 and 68 with adhesive means to form the V-shaped portion 40 and the overall conical structure of the pad.

Alternate means for forming the V-shaped portion may also be used. For example, without slitting, the material may be gathered together, overlapped and sewn in place to form a V-shaped portion 40 having three times the number of layers of the main body portion 32. Alternatively, a V-shaped wedge may be removed from the layers and a separate suitably sized V-shaped portion sewn therein. However, in the illustrated preferred embodiment, the overlapped V-shaped portion spans an arc of approximately 60° as illustrated by the circular pads 30a and 30b. This forms a conical structure which advantageously conforms to nearly any sized breast and does not bunch or wrinkle when worn, but rather lays flat and discreet under a woman's clothing.

In operation, the nursing pad 30 may be used by a lactating woman or a woman during the latter stages of her pregnancy to absorb milk excretion from the woman's nipples. The outer convex surface 52 may be placed adjacent an interior surface of a cup-like portion of a bra-like garment. The inner surface 54 is placed adjacent the woman's skin with the apex 32 located approximately over the woman's nipple. Note that the term bra or bra-like garment may not only include a conventional woman's brassiere, but may also include a nursing bra or other garments having a bra-like portion formed therein, such as a swimsuit or a strapless evening gown. Since the force of gravity tends to draw excreted milk downward, the pad may be rotated such that the V-shaped portion 40 lies along the underside of a woman's breast to provide additional absorbency in this area. After use, the nursing pads 30b, 30d and 30e may be disposed of, whereas the fabric pads 30a, 30c and 30e may be laundered and reused. The outer boundary stitching 60 helps the fabric pads maintain their shape through repeated launderings.

Having illustrated and described the principles of my invention with respect to the preferred embodiments, it should be apparent to those skilled in the art that my invention may be modified in arrangement and detail without departing from such principles. For example, the apex 34 may not be concentric to the pad, or the outer boundary 36 of the pad may take on different shapes, such as rectangular, pentagonal, or other shapes, to accommodate the style or fashion of a woman's clothing or her personal preferences. Also, the nursing pad 30 may include an outer layer 52 of a moisture-impervious material, or a semi-moisture-impervious material. Furthermore, suitable material substitutions and dimensional variations for the components of the pad may also be implemented.

I claim:

1. A nursing pad for placement inside a cup-like portion of a bra-like garment, the nursing pad comprising:
   a plurality of layers of an absorbent material, each of the layers having a generally circular periphery and a center with a radial cut extending therebetween, the layers being superimposed upon each other with the radial cuts in register, each cut in each layer forming a first and a second radial edge, the first radial edges of all the layers being rotated about the centers of the layers to overlap the second radial edges thereof to form a conical structure having a generally isosceles triangular area with double the number of layers of material, said radial edges forming the legs of the isosceles triangular area; and attachment means for attaching all the layers together as a unit at least along both the legs of the isosceles triangular area, said conical structure having an outer boundary, an outer convex surface and an inner concave surface, whereby the nursing pad outer convex surface may be placed adjacent an interior surface of the cup-like portion of the bra-like garment for use by a wearer of the garment to absorb discharge of milk from the wearer.

2. A nursing pad according to claim 1 wherein the attachment means comprises threaded stitching means.

3. A nursing pad according to claim 2 wherein the absorbent material comprises layers of fabric, and the nursing pad further includes boundary threaded stitching means extending around the outer boundary of the conical structure for securing together and for retarding unraveling of the layers of fabric.

4. A nursing pad according to claim 3 wherein the layer of fabric material at the inner concave surface comprises a soft flannel material.

5. A nursing pad according to claim 3 wherein the layer of fabric material at the outer convex surface comprises a birdseye weave material.

6. A nursing pad according to claim 1 wherein the outer boundary is substantially circular in shape.

7. A nursing pad according to claim 1 wherein the outer boundary has a substantially elliptical shape defining mutually perpendicular longitudinal major and transverse minor diameters, and the generally triangular area is symmetrical about the transverse minor diameter.

8. A nursing pad according to claim 1 wherein the outer boundary has a substantially elliptical shape defining mutually perpendicular longitudinal major and transverse minor diameters, and the generally triangular area is symmetrical about the longitudinal major diameter.

9. A nursing pad according to claim 1 wherein the absorbent material comprises layers of an absorbent paper-like material, whereby the nursing pad may be disposed of after use.

10. A nursing pad according to claim 1 wherein the plurality of layers comprises between four layers and eight layers.

11. A nursing pad according to claim 1 wherein each of the layers has a segment removed from its periphery and the radial cut extends from an end of the segment.

12. A nursing pad according to claim 1 wherein the generally isosceles triangular area comprises an isosceles triangle of about 60 degrees.

13. A nursing pad for placement inside a cup-like portion of a bra-like garment, the nursing pad comprising:

a plurality of layers of an absorbent material, each of the layers having a generally circular periphery and a center, the layers having a defined radius extending between the periphery and the center, all the layers being gathered together as a unit at the defined radius and rotated about the center to overlap a portion of the layers and form a conical structure having a generally isosceles triangular area with three times the number of layers of material, the defined radius forming one of the legs of the isosceles triangular area; and attachment means for attaching all the layers together as a unit at least along both the legs of the isosceles triangular area, said conical structure having an outer boundary, an outer convex surface and an inner concave surface, whereby the nursing pad outer convex surface may be placed adjacent an interior surface of the cup-like portion of the bra-like garment for use by a wearer of the garment to absorb discharge of milk from the wearer.

* * * * *